United States Patent [19]

Ammerman

[11] Patent Number: 4,723,974

[45] Date of Patent: Feb. 9, 1988

[54] TRANSPORTING CONTAINER FOR AN AMPUTATED EXTREMITY

[76] Inventor: Stephen W. Ammerman, 370 Lower Lake Rd., Lake Sherwood, Calif. 91361

[21] Appl. No.: 900,675

[22] Filed: Aug. 27, 1986

Related U.S. Application Data

[63] Continuation-in-part of Ser. No. 759,336, Jul. 26, 1985, abandoned.

[51] Int. Cl.$^4$ .............................................. F25D 5/00
[52] U.S. Cl. ......................................... 62/4; 62/371; 62/457; 62/530
[58] Field of Search ................. 206/205; 62/294, 457, 62/306, 463, 371, 530, 4

[56] References Cited

U.S. PATENT DOCUMENTS

| | | | |
|---|---|---|---|
| 2,880,856 | 4/1959 | Albrecht | 62/457 X |
| 2,916,886 | 12/1959 | Robbins | 62/294 X |
| 3,298,194 | 1/1967 | Hutchinson | 62/294 |
| 3,810,367 | 5/1974 | Peterson | 62/463 X |
| 3,887,346 | 6/1975 | Erdman | 62/4 |
| 3,893,834 | 7/1975 | Armstrong | 62/4 |
| 3,950,158 | 4/1976 | Gossett | 62/4 |
| 3,970,068 | 7/1976 | Sato | 62/294 X |
| 4,502,295 | 3/1985 | Toledo-Pereyra | 62/306 X |
| 4,530,816 | 7/1985 | Douglas-Hamilton | 62/463 X |

FOREIGN PATENT DOCUMENTS 494112  10/1938  United Kingdom ................. 62/463

*Primary Examiner*—Lloyd L. King
*Attorney, Agent, or Firm*—Jack C. Munro

[57] ABSTRACT

A container assembly to provide a cooling environment for a severed extremity to facilitate transporting of the extremity to a hospital or other similar location for the purpose of facilitating replantation of the extremity to the patient. The container assembly provides for a flexible walled inner container mounted inside of a flexible walled outer container. A single access opening facilitates entry only into the inner container. The inner container is adapted to receive the severed extremity as well as a quantity of saline solution or the extremity wrapped with a cloth soaked with the saline solution. There is an outer container located around the inner container. Within the outer container is located a chemical cooling medium that, when activated, causes a significant reduction in temperature of the environment located within the inner container.

2 Claims, 7 Drawing Figures

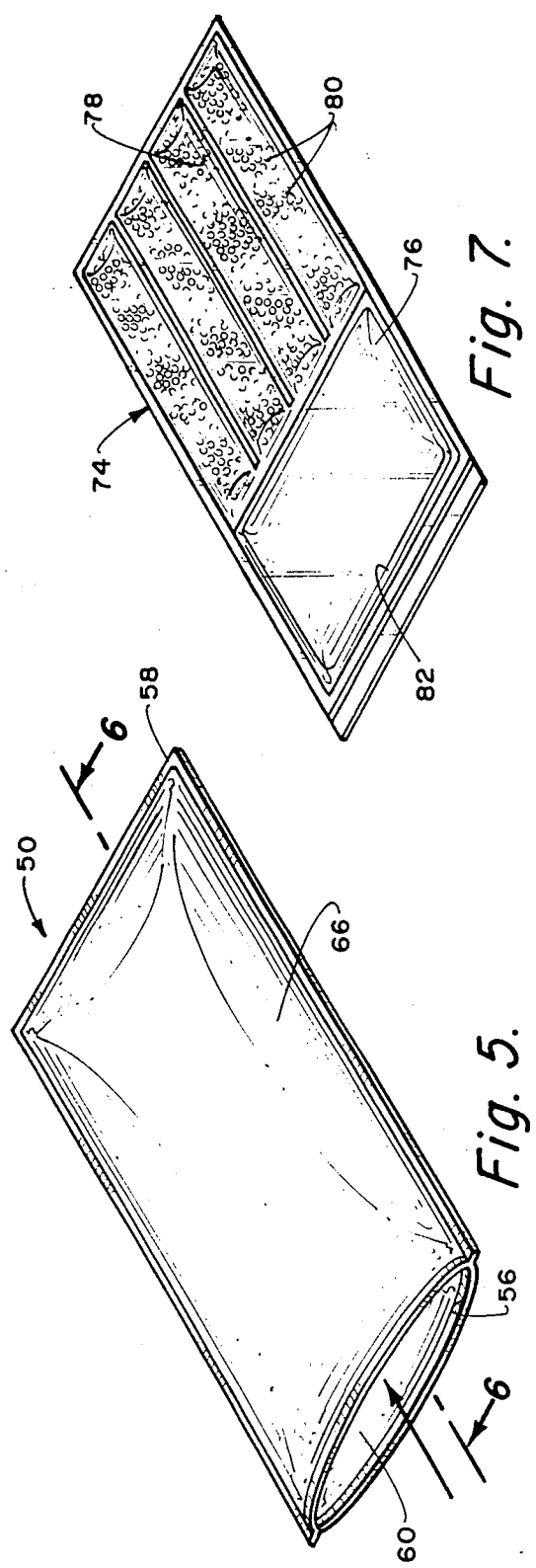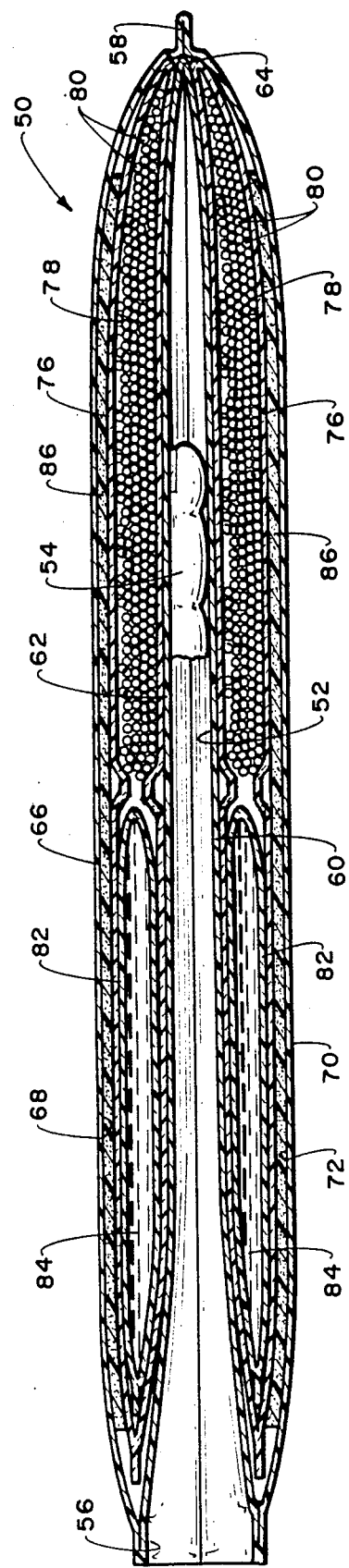

TRANSPORTING CONTAINER FOR AN AMPUTATED EXTREMITY

REFERENCE TO PRIOR APPLICATION

This application is a continuation-in-part of patent application Ser. No. 759,336, filed July 26, 1985, now abandoned, by the same inverter and by the same title.

BACKGROUND OF THE INVENTION

The field of this invention relates to medical products, and more particularly to a disposable container assembly which provides a cooling environment to a severed extremity to facilitate transporting of the extremity to a hospital for the purpose of replantation.

Amputations of extremities of human beings are a common form of medical emergencies. People that work with machines, such as farm workers, industrial workers and mechanics, are constantly susceptible to the possibility of an amputation. Also, amputations do occur within automobile and motorcycle accidents as well as home accidents caused by lawn mowers or saws. Common types of amputations are fingers, hands, forearms, ears, feet, legs, nose and even possibly the penis.

In recent years, the medical profession has discovered that it is possible to replant the amputated part. Time is the enemy for accomplishing satisfactory replantation. It has been found that in order for the amputated part to re-achieve maximum function, it must be replanted within a three hour period if the part is maintained at normal room temperature. If the part is located in a cooling environment, the time period can be extended to six hours. However, even some function can be obtained in replanting of an uncooled part up to six to eight hours, and a cooled part up to twenty-four hours.

Paramedics and other emergency medical personnel encounter amputated extremities while in the field. These medical personnel have been counseled to clean the amputated part with a saline solution and wrap such in a sterile towel again moistened with the saline solution. The amputed part is then enclosed within a plastic bag which is to be placed in a cold environment such as ice or ice water. However, the ice water is not to come into direct contact with the amputated part.

At the present time, medical emergency personnel are required to carry transport portable ice chests which are constantly maintained in ready state to be instantaneously available during an emergency call. Up until the present invention, there has not been any known structure which has been designed specifically for the purpose of locating of an amputated extremity within a decreased temperature environment to facilitate transfer of such to a hospital or other similar location for replantation.

SUMMARY OF THE INVENTION

The structure of the present invention relates to a container assembly composed of an inner container and an outer container. Both containers have flexible walls in order to facilitate storage when not in use, transportability and usage. The container assembly is adapted to receive the amputated extremity. Within one embodiment of this invention, the extremity is located within a quantity of a liquid such as a saline solution. Within another embodiment, the inner extremity wrapped in a cloth impregnated with a saline solution. The inner container of the first embodiment would be closable in a liquid tight manner by a disengageable fastener. There is a cooling compartment provided around the inner compartment within which is located a quantity of a cooling medium. A desirable form of cooling medium would be a chemical composition which can be manually activated. Covering exteriorly the cooling compartment is an insulating layer.

The primary objective of the present invention is to construct an inexpensive kit which can be transported by any emergency vehicle to any remote location which facilitates temporary storage of a severed extremity and maintains such in a low temperature environment for a limited period of time.

BRIEF DESCRIPTION OF THE DRAWINGS

FIG. 5 is an isometric view of a second embodiment of the container assembly of the invention showing the container assembly open to receive the amputated extremity;

FIG. 6 is a cross-sectional view taken along line 6—6 of FIG. 5; and

FIG. 7 is an isometric view of one of the chemical cooling packs utilized within the container assemlby of FIG. 5.

DETAILED DESCRIPTION OF THE SHOWN EMBODIMENTS

Figure 1:
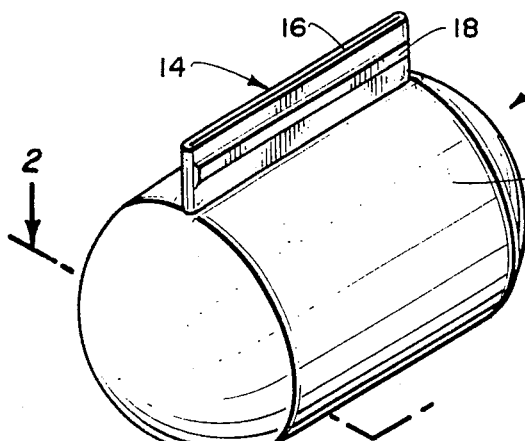
FIG. 1 is an exterior isometric view of the first embodiment of the container assembly of the present invention showing the container assembly in the closed position.
Figure 3:
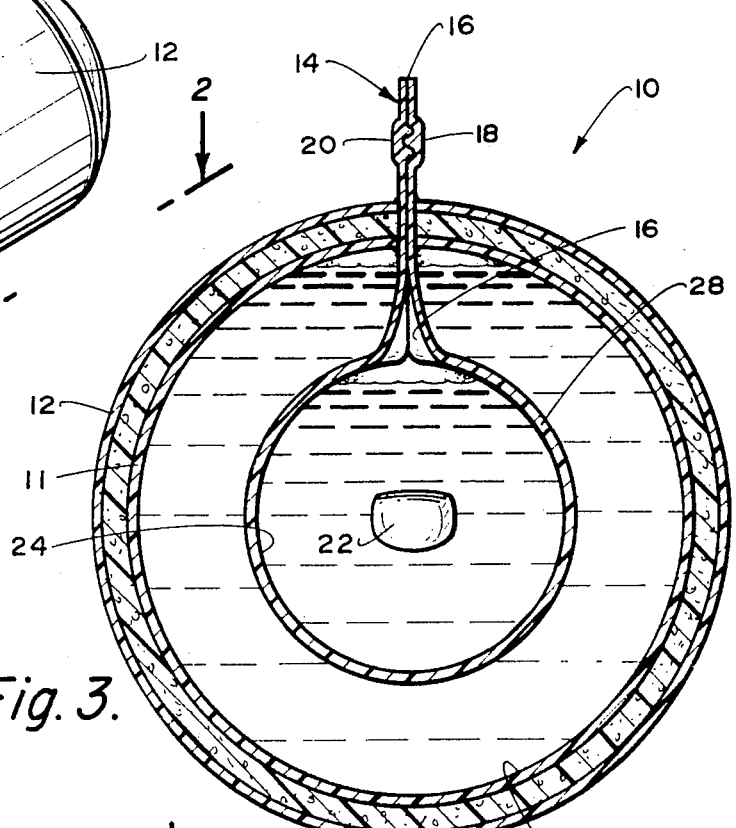
FIG. 3 is a cross-sectional view taken along line 3—3 of FIG. 2.
Figure 2:
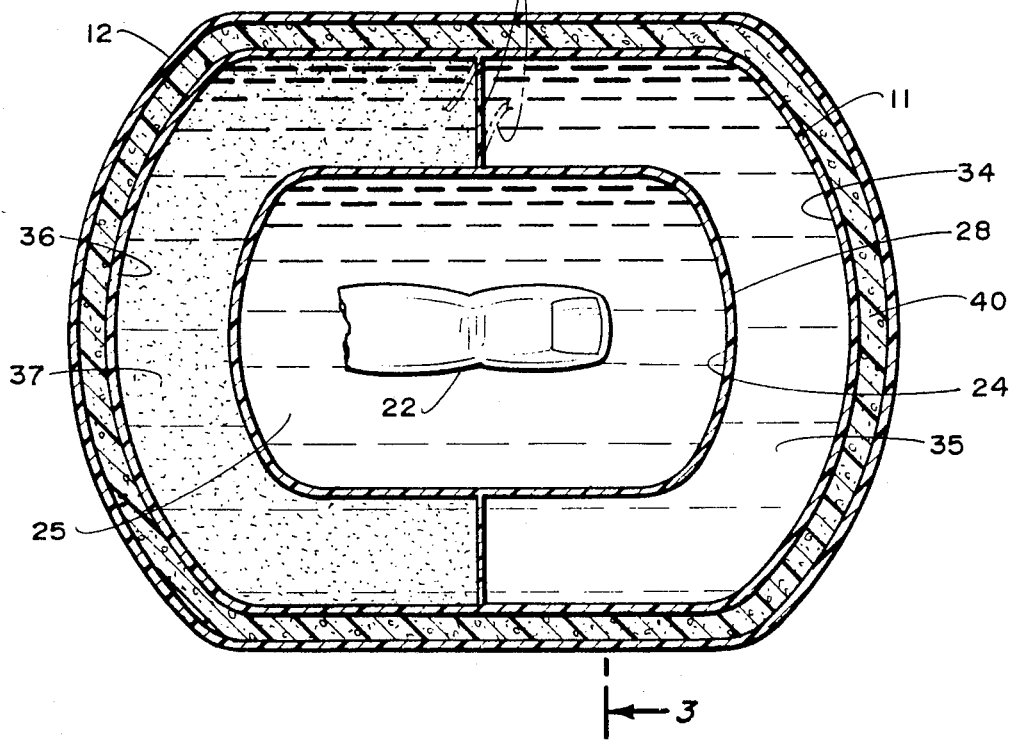
FIG. 2 is a cross-sectional view taken along line 2—2 of FIG. 1 depicting the container assembly in the closed position containing a single amputated extremity.

Referring particularly to the drawings, there is shown in FIGS. 1 to 3 the container assembly 10 of the present invention which is composed generaly of a flexible walled outer container 11. The flexible walled container will be totally constructed of a sheet material such as plastic or other similar material. The outer container 11 is covered exteriorly by a foam insulating layer 40. There may be included on the exterior surface of the plastic foam insulating layer 40 a protective plastic cover layer 12. The foam layer 40 will normally be adhesively adhered to the wall 11. Also, the protective cover 12 will normally be adhesively secured onto the exterior surface of foam layer 40. Both the foam insulating layer 40 and the protective cover 12 are to be flexible.

The container 11 includes an enlarged interior compartment which is divided into a pair of compartments 34 and 36. As is seen in FIG. 3 of the drawings, the transverse cross-sectional shape of the compartments 34 and 36 is circular. Centrally positioned within the compartments 34 and 36 is a flexible wall 28 of an inner container. Normally the material of construction of the wall 28 will be identical to the material of construction of the wall 11.

Inner container 28 includes an interior compartment 24. The interior compartment 24 is capable of containing a liquid solution, such as a saline solution 25. The saline solution 25 may or may not be used. In lieu thereof the amputed extremity 22 may be wrapped with a saline impregnated gauze and just located within the interior compartment 24.

The compartments 34 and 36 are divided by a frangible separating wall 38. Compartment 34 is designed to contain one part of a cooling medium such as water. Compartment 36 is designed to contain a quantity of another part of a cooling medium such as ammonium nitrate as well as other substances such as calcium carbonate, starches and so forth. When it is desired to activate the cooling medium, the operator physically deforms the container assembly 10 causing breaking of the wall 38 which will then result in mixing together of chemical substances 37 located within compartment 34 and the chemical substance 37 located within the compartment 36. This mixing together of the substances produces a significantly decreased temperature such as approximately forty degrees Fahrenheit. This decrease in temperature cannot be readily perceived by touching the cover 12. However, the breaking of the frangible wall 38 can be easily detected by feel and observation by the individual breaking of the wall 38. The mixing of the substances 35 and 37 is accomplished by squeezing alternately a plurality of times the compartments 34 and 36 to effect mixing of the substances 35 and 37. This decrease in temperature, though not felt exteriorly, will cause the saline solution 25 to also be lowered to a similar temperature which will then cause similar reduction in temperature of the amputated extremity 22.

In order to gain access into the interior compartment 24 so as to locate the amputated extremity 22 within the compartment 24 and effect removal thereof, there is incorporated a disengageable liquid-tight fastener assembly 14. The fastener assembly 14 is constructed of a pair of flanges 18 and 20. The flanges 18 and 20 have inner surfaces which are to be connectable together in a tight inner fitting manner in order to produce a liquid-tight seal. The flanges 18 and 20 can be manually separated, spreading apart in the middle, to form an opening 16 to gain access into and out of internal compartment 24. This enlarging of the opening 16 is permitted due to the flexibility of the cover 12, the insulating layer 40 and the container 11. It is to be understood that the flanges 18 and 20 can be re-engaged to close the gap 16 as is clearly shown within FIG. 3 of the drawings. It is to be understood that numerous types of disengageable fastening means could be utilized such as a structure resembing a conventional zipper.

Figure 4:
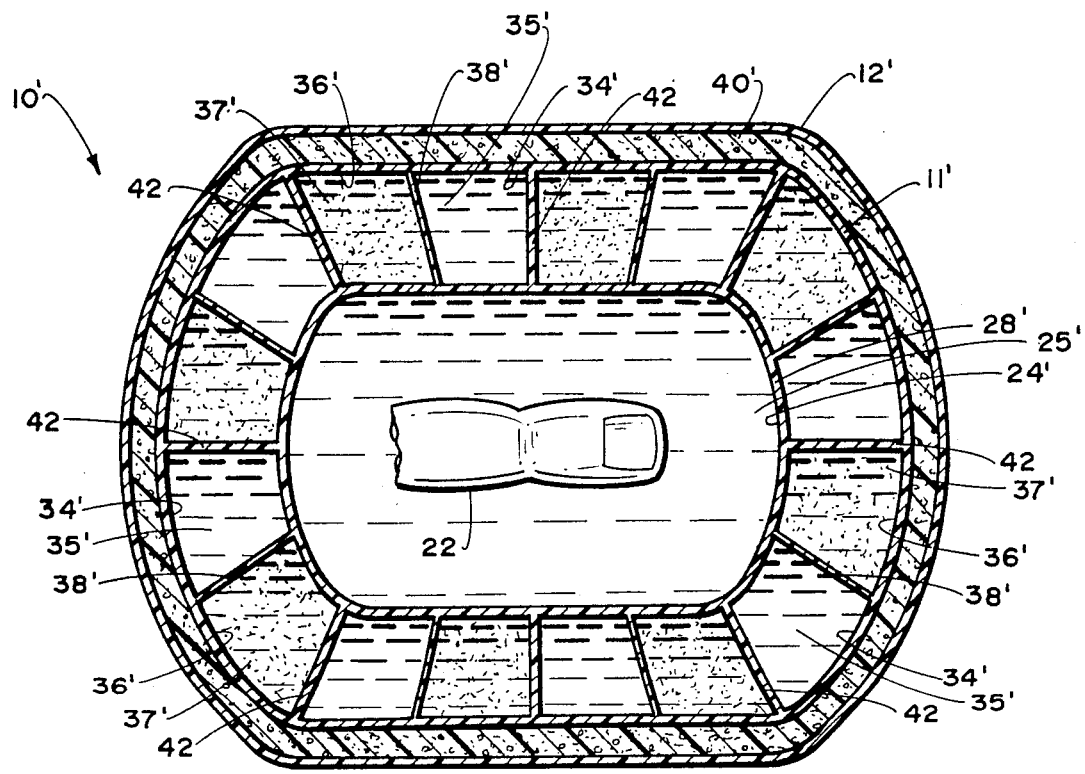
FIG. 4 is a cross-sectional view, similar to FIG. 2, but showing a modified form of the container assembly of this invention which utilizes a plurality of cooling compartments instead of a single cooling compartment.

Referring particularly to FIG. 4 of the drawing, there is shown a modified version 10' container assembly of this invention. The container assembly 10' is formed in substantially the same manner as container assembly 10 and like numbers have been used to refer to like parts. Container assembly 10' includes an outer protective cover 12' which is attached onto insulating layer 40'. Insulating layer 40' is adhered to wall 11'. Inwardly of wall 11' is formed an annular space which is divided into compartment 34' and 36'. Separating the compartments 34' and 36' are walls 38' and 42. Between each directly adjacent pair of walls 42 there is confined a compartment 34' and a compartment 36'. Only the wall 38' separating the compartments 34' and 36' is frangible. Walls 42 are not frangible. Again, compartment 34' is to contain one type of liquid, such as water 35', while compartment 36' is to contain another type of liquid, such as ammonium nitrate 37' as well as other substances. The user may optionally break one or more of the frangible walls 38' at spaced time intervals in order to achieve a timed release of a decreased temperature through wall 28' to be conducted into saline solution 25' to lower the temperature of the amputated extremity 22'. The user is able to determine by "touch" whether a wall 38' is broken or unbroken. The user also will have instructions to know how often to break a wall 38' to maintain adequate cooling. It can be seen within FIG. 4 that there are eight pairs of the compartment 34' and 36'. This paired arrangement of compartments can be increased in number or decreased in number without departing from the scope of the structure shown in FIG. 4.

It is to be understood that access within the compartment 24' is to be provided in a manner similar to the liquid-tight fastener 14 shown within FIGS. 1 through 3 of the drawings. Also, the container assembly of this invention will be manufactured in various sizes to accommodate various sizes of extremities.

Referring particularly to FIGS. 5, 6 and 7 of the drawings there is shown a second embodiment of the container assembly 50 of this invention which basically assumes a flat, envelope shape configuration. Container assembly 50 has an inner compartment 52 within which is to be located the amputated extremity 54. Insertion of the extremity 54 into the inner compartment 52 is completed through access opening 56 located within the front end of the container assembly 50. The aft end of the container assembly 50 is sealed and therefore completely closed by sealing strip 58. Sealing strip 58 also extends aong each of the side walls of the container assembly 50.

The inner compartment 52 is encased by plastic sheet material upper and lower walls 60 and 62. The walls 60 and 62 are sealed together at their sides and are folded over upon themselves at the end joint 62. The wall 62 is enclosed by an exterior wall 66 forming an outer compartment 68. The wall 60 is enclosed by means of an exterior wall 70 forming an outer compartment 72.

Within the outer compartment 68 there is to be located a cooling pack 74. A similar cooling pack 74 is to be contained within the outer compartment 72. Each cooling pack 74 is a self-contained unit comprising a closed exterior wall 76 again formed of a plastic or other similar type of material. The lower end of each cooling pack 74 is divided into a series (actually four in number being shown) of elongated chambers 78. Within each of the chambers 78, there is to be located a quantity of pelletized or granulated ammonium nitrate material 80.

The upper end of each of the chambers 78 includes a bag 82. Within each bag 82 there will be located a liquid such as a water 84 or other similar type of desirable liquid composition. Squeezing of the bags 82 will result in breaking of such and the liquid 84 intermixes with the material 80. As a result, a cooling chemical reaction is produced. Because there are a plurality of the chambers 78 utilized, the collecting of the material 80 into one particular location is prevented, thereby evenly distributing the cooling affect across the width of the container assembly 50. This is desirable in order to prevent "hot spots" in which certain areas of the inner compartment 52 would not be adequately cooled.

It is to be noted that the wall surfaces of the entire container assembly 50 are constructed of a transparent plastic material. However, it is considered to be within the scope of this invention that an opaque plastic could be utilized. In order to assist in confining of the cooling affect to the inner compartment 52, there would be utilized a foam insulative pad 86 located between the cooling bag 74 and the wall 66 and also between the cooling bag 74 and the wall 70.

After the extremity 54 is located in position within the inner compartment 52, the edges of the access opening 56 are closed together and folded over against either wall 66 or 70. When so folded over, there will usually be incorporated some type of fastening device (not shown) to hold such in position with a common form being a wire tie located on each side of the wall of the access opening 56.

What is claimed is:

1. A container assembly for transporting of an amputated extremity to a location for replantation, said container assembly comprising:

an inner compartment adapted to receive an amputated extremity, said inner compartment being defined by a wall, an acess opening providing access into said inner compartment, said access opening being closable;

a completely closed outer compartment surrounding said inner compartment, said outer compartment abutting said wall; and a plurality of cooling bags located within said outer compartment, each said cooling bag containing a pair of substances when mixed results in the production of a cooling affect, each said cooling bag containing a plurality of chambers, said chambers being connected but separate, one of said substances being a granulized solid, said granulized solid being located within said separate chambers, whereby upon mixing occurring of said substances substantially even distribution of the cooling affect is obtained across the entire width of said inner compartment due to mixing between said substances occurring within each said chamber.

2. The container assembly as defined in claim 1 including:

a foam insulating layer located between each said cooling bag and the exterior wall of said outer compartment.

* * * * *